United States Patent [19]

Jannard

[11] Patent Number: 4,824,233
[45] Date of Patent: * Apr. 25, 1989

[54] MULTI-COMPONENT SUNGLASSES

[76] Inventor: James H. Jannard, 30741 Fox Run La., San Juan Capistrano, Calif. 92675

[*] Notice: The portion of the term of this patent subsequent to Jun. 23, 2004 has been disclaimed.

[21] Appl. No.: 156,352

[22] Filed: Feb. 11, 1988

Related U.S. Application Data

[60] Division of Ser. No. 787,242, Oct. 15, 1985, Pat. No. 4,730,915, which is a continuation-in-part of Ser. No. 690,642, Jan. 11, 1985, Pat. No. 4,674,851.

[51] Int. Cl.⁴ .............................................. G02C 9/00
[52] U.S. Cl. ...................................... 351/47; 351/44; 351/116
[58] Field of Search ...................... 351/41, 44, 47, 57, 351/116

[56] References Cited

U.S. PATENT DOCUMENTS

| | | |
|---|---|---|
| 145,288 | 7/1946 | Di Cicco . |
| 163,869 | 7/1951 | Hinman . |
| 176,316 | 12/1955 | Fleming . |
| 178,178 | 7/1956 | Fleming . |
| 187,394 | 3/1960 | Moeller . |
| 199,150 | 9/1964 | Carmichael . |
| 210,048 | 1/1968 | Imperatrice . |
| 268,683 | 4/1983 | Tenny . |
| 285,020 | 9/1986 | Schmidthaler . |
| 2,444,498 | 7/1948 | Cochran . |
| 2,472,731 | 6/1949 | Splaine . |
| 2,482,664 | 9/1949 | Gagnon . |
| 2,582,345 | 1/1952 | Moeller . |
| 3,133,982 | 5/1964 | Janz . |
| 3,233,249 | 2/1966 | Baratelli et al. . |
| 3,233,250 | 2/1966 | Jonassen . |
| 3,531,189 | 9/1970 | Petito . |
| 3,689,136 | 9/1972 | Atamian . |
| 3,708,224 | 1/1973 | Linblom . |
| 3,756,704 | 9/1973 | Marks . |
| 4,515,448 | 5/1985 | Tackles . |
| 4,564,272 | 1/1986 | Kan . |
| 4,730,915 | 3/1988 | Jannard ................................ 351/47 |

FOREIGN PATENT DOCUMENTS

| | | |
|---|---|---|
| 673815 | 1/1930 | France . |
| 790755 | 11/1935 | France . |
| 2472764 | 7/1981 | France . |

OTHER PUBLICATIONS

Picture of Oakley Blades as first worn 8/27/85.

Primary Examiner—Rodney B. Bovernick
Assistant Examiner—P. M. Dzierzynski
Attorney, Agent, or Firm—Knobbe, Martens, Olson & Bear

[57] ABSTRACT

Disclosed is a pair of sunglasses having a unitary transparent pane extending in a curved pane and over the wearer's nose bridge. The sunglasses frame and nose piece construction permits their ease of removal and replacement, as well as pane replacement, and provision is made for stem pull-away, frame padding and elastomeric pads to engage the sides of the wearer's nose.

9 Claims, 3 Drawing Sheets

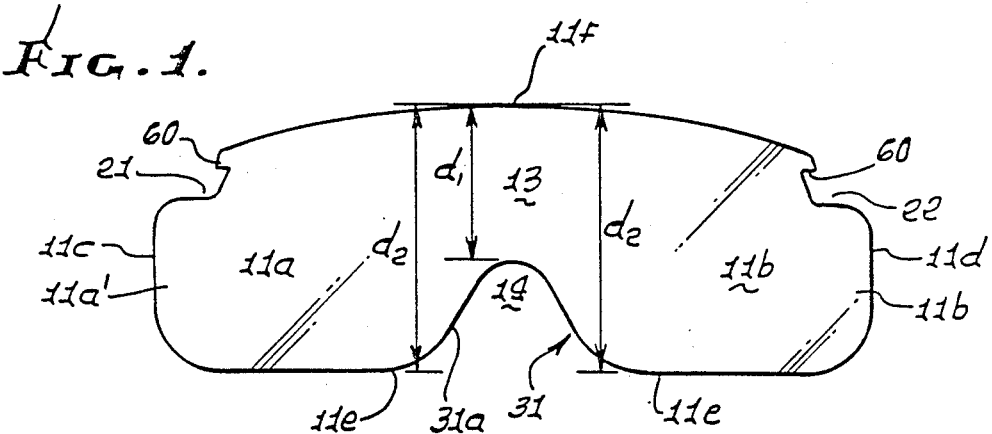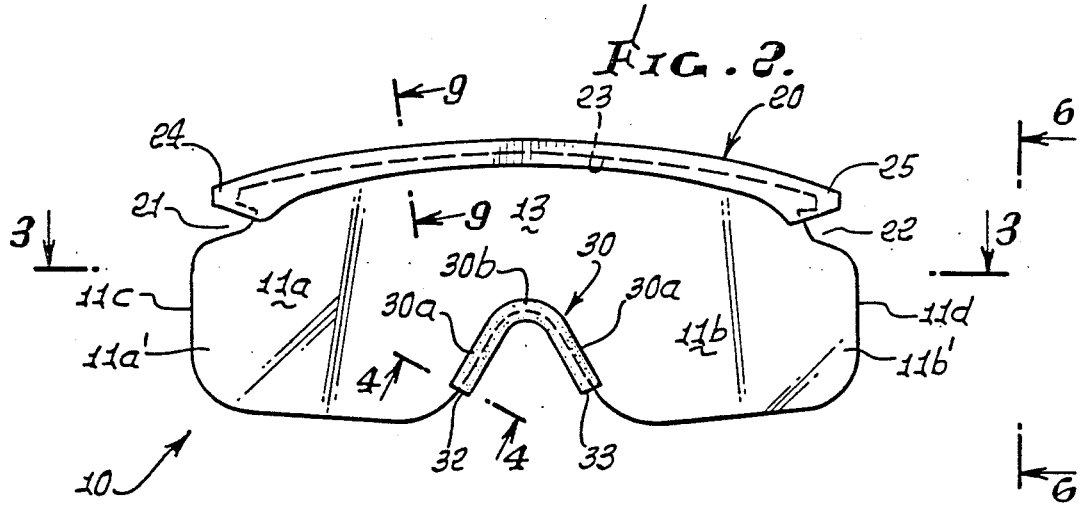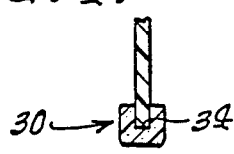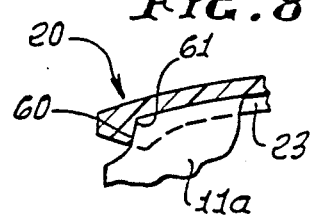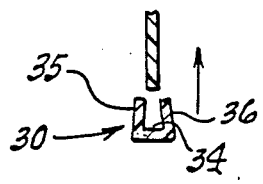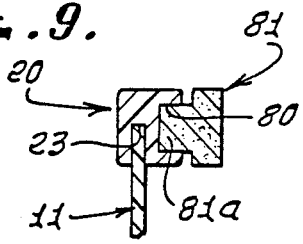

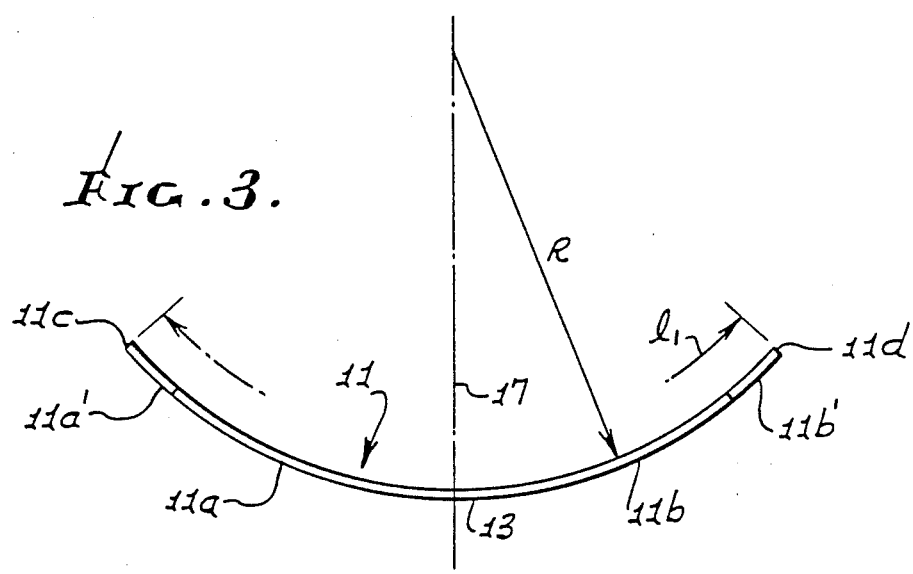
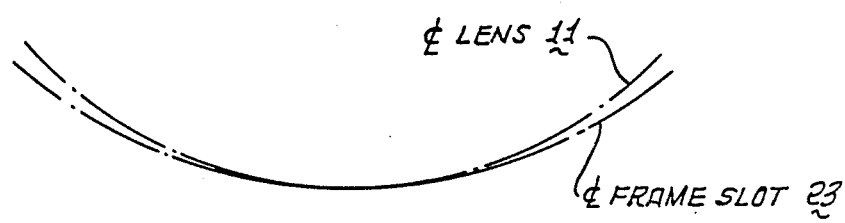
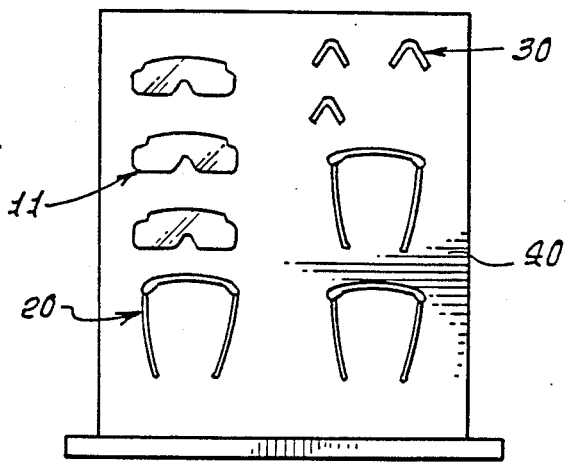

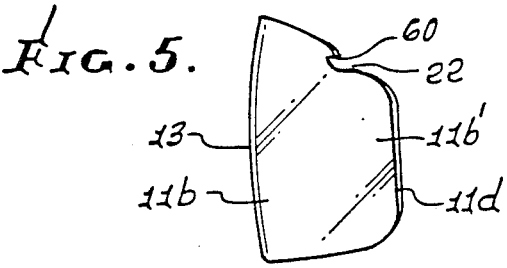
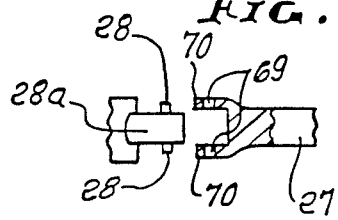
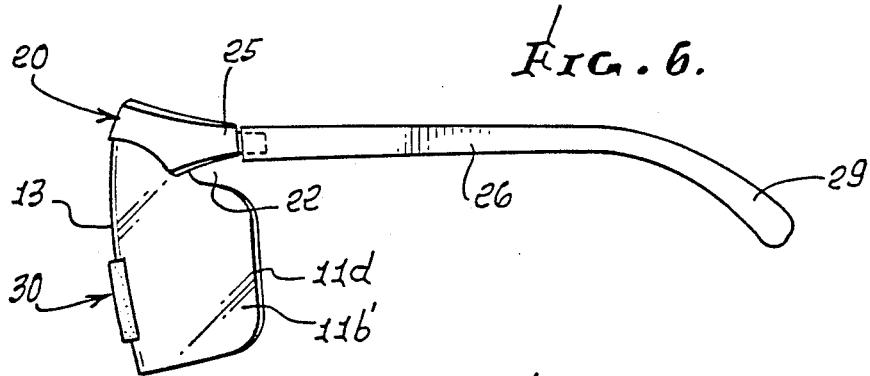
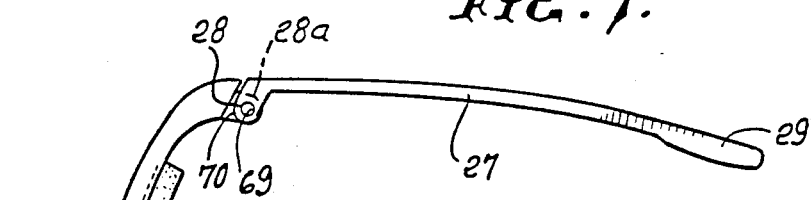
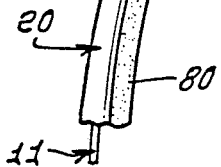
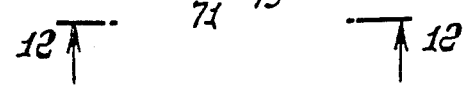
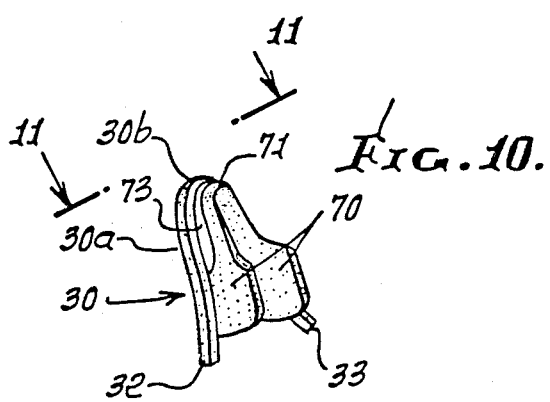

MULTI-COMPONENT SUNGLASSES

BACKGROUND OF THE INVENTION

This application is a division of Ser. No. 787,242, filed Oct. 15, 1985, which is now U.S. Pat. No. 4,730,915. The '915 patent is a continuation-in-part of Ser. No. 690,642, filed Jan. 11, 1985. This invention relates generally to eyewear, and more particularly to construction of sunglasses.

There is a need for sunglasses which more completely intercept sunlight at the top, bottom and sides of the glasses; also, there is need for sunglasses which permit of pane or lens removal and replacement, and also replacement or substitution of different nose pieces and frames, to better fit the wearer. There is also need for simplicity of frame, nose piece and lens assembly construction, together with means to reduce air turbulence and moisture on the lens, near the eyes of the wearer, and for stem pull-away.

SUMMARY OF THE INVENTION

The eyeglasses of the present invention comprise a unitary transparent lens or pane located to extend in the paths of the wearer's fields of vision, frontwardly and sidewardly, and the lens extends in a pane which may be frusto-conical when attached to the frame, partially wrapping around the sides of the head to intercept peripheral vision. The result is better interception of sunlight, top-to-bottom and side-to-side, the lens matching closely the wearer's facial contour. No distortion is introduced because of the absence of sudden changes in the rate of curvature or breaks in shape.

As will be seen, the protective eyeglasses or sunglasses basically comprise a unitary transparent pane located to extend in a curved pane in the path of the wearer's field of vision, both frontally and sidewardly, and having an upwardly humped lower edge which bounds a space to receive the wearer's nose. A top frame extends along and bounds the upper edge extent of the pane, and arms or stems attached to the top frame at opposite ends thereof are provided with "pull-free" construction, and are adapted to extend rearwardly to the wearer's ears. A nose piece is provided which bounds the upwardly humped lower edge of the unitary pane, and having elastomeric pads to engage the nose. At least one of the top frame or the nose piece are removably attached to the unitary pane.

As will be seen, typically both the top frame and nose piece are removably attached to the unitary pane, such attachments being independent to permit selective removal and replacement of the nose piece and top frame, as well as the pane itself. The wearer can thereby easily assemble eyeglasses from a group of components of different sizes, to best fit his or her facial and head contours. Preferably, the curved pane is substantially cylindrical in the as-molded condition, but deformed slightly by its cooperation with a slot in the top frame to have a slight frusto-conical curvature, and it optimally consists of a synthetic resin.

The present invention further provides a replaceable nose piece including nose engaging pads that consist of a relatively soft elastomeric material having a coefficient of sliding friction that increases when the material is wetted, such material typically being hydrophilic. Foam padding may be carried by the top frame to engage the wearer's forehead.

The sunglasses of the present invention have a unitary lens pane free of frame structure along the frame side edges which extend downwardly from locations proximate the attachment of the ear stems to the top frame, and then inwardly along the base edge toward the nose piece terminals. The top frame is removable relatively upwardly off the unitary pane, and the nose piece is removable relatively downwardly from the unitary pane. As will be seen, the unitary pane may have tang means to interfit the frame.

These and other advantages of the invention, as well as the details of the illustrative embodiment, will be more fully understood from the following specification and drawings.

BRIEF DESCRIPTION OF THE DRAWINGS

FIG. 1 is a front view of a unitary pane in flattened condition;

FIG. 2 is a frontal view of sunglasses incorporating the invention;

FIG. 3 is a section through the cylindrically normal pane on lines 3—3 of FIG. 2;

FIG. 4 is an enlarged section on lines 4—4 of FIG. 2, and FIG. 4a is like FIG. 4 prior to assembly of the nose piece to the pane;

FIG. 5 is a side view of the curved pane in as-molded condition;

FIG. 6 is a side view of the assembled sunglasses on lines 6—6 of FIG. 2;

FIG. 6a is an inner side view of the ear stem detached from the top frame;

FIG. 7 is a top plan view showing frame and stem hinge structure and padding;

FIG. 8 is an enlarged fragmentary section showing tang interfit of the unitary pane and top frame;

FIG. 9 is an enlarged section taken on lines 9—9 of FIG. 2 to show frame slots for both the pane and padding;

FIG. 10 is a perspective view of a nose piece with attached elastomeric pads to engage the sides of the wearer's nose;

FIG. 11 is a top plan view on lines 11—11 of FIG. 10;

FIG. 12 is a front view on lines 12—12 of FIG. 11;

FIG. 13 is a diagram to show mismatch between interfits of the pane and top frame; and FIG. 14 is a display.

DETAILED DESCRIPTION OF PREFERRED EMBODIMENTS

The protective eyeglasses, as for example, sunglasses shown at 10 in FIG. 2, include transparent panes or lenses 11a and 11b located to extend in the direct path of the wearer's left and right eye fields of vision. Those panes merge as at bridge 13 directly above the wearer's nose, a generally triangular nose opening being formed at 14. (FIG. 1). Thus, a unitary or single pane or lens 11 is provided and may be easily replaced, as for example, by panes of lesser or greater darkness, size or different coloring, etc., as desired by the wearer.

It is a feature of the invention that the unitary pane extends in a pane which is substantially and preferably precisely cylindrical in as-molded condition. FIG. 3 shows the cylindrical curvature of the single pane, and between opposite end wings 11a', and 11b'. FIG. 1 shows the pane in flattened condition, i.e., pressed into the flat plane of the paper. The panes 11a and 11b and bridge 13 are formed to have cylindrical conformation which becomes frusto-conical when the pane is attached to top frame 20, such that their curvatures conform very well to the natural curvature of the wearer's face, i.e., his cheek bones and forehead, as well as side face configuration. Note that panes 11a and 11b and wings 11a, and 11b, wrap backwardly or rearwardly to extend in the paths of the wearer's sideward fields of vision, without such abruptly changing curvature as would distort the light passing through the side wrapping portions of the panes. Referring to FIG. 3, the curved planes of panes 11a and 11b are symmetrically located at opposite sides of a plane 17 bisecting the bridge 13, and contained by the axis of the cylinder defined by the panes. For best results, the radius R of curvature of the panes is in the range of 3.25 to 5 inches, and optimally within the range of 3.50 and 4 inches.

As illustrated in FIG. 1, the pane 11 has a vertical dimension $d_1$ immediately above the nose bridge, $d_1$ being between 0.75 and 1.50 inches. In addition, the pane has generally rearwardly extending lateral terminals 11c and 11d, and a length dimension $l_1$ between said terminals, $l_1$ being between about 5.50 and 7 inches, as measured along the cylindrical curvature of the pane. The pane has two lowermost terminals 11e, and vertical dimensions $d_2$ between 2 and 2.75 inches, as measured between those lowermost terminals 11e and the pane uppermost top edge 11f.

Also provided is a top frame 20 extending along and bounding the upper edge extent of the lens or pane 11, as between the notched areas 21 and 22 formed immediately above the wings 11a' and 11b'. The frame may advantageously consist of relatively rigid, molded plastic material which may be transparent. The top frame is shown as being removably attached to the top edge extent of the lens or pane and, for this purpose, a slot 23 (see FIGS. 2 and 9) is formed upwardly therein from the bottom of the frame 20, with curvature generally matching that of the lens to tightly, yet removably receive the upper edge extent of the lens. For this purpose, the curvature of the slot 23 may be slightly different than the cylindrical, as-molded curvature of the lens to provide a mismatch to grip the pane, which then resiliently co-acts with the frame to slightly deform the pane to frusto-conical shape (see FIG. 13). Note that the upper edge 11f of the lens is shown to have slight upward convexity (FIG. 1), as well as cylindrical curvature (FIG. 3).

Tang means such as one or more tangs 60 integral with the pane and projecting over notched areas 21 and 22 rearwardly fit in corresponding shallow recesses 61 in the frame at opposite ends of the slot 23 to help retain the pane in position (see FIGS. 1, 2, 5 and 8).

The top frame has enlarged end terminals at 24 and 25 that extend in notched areas 21 and 22, and are pivotally attached to two stems or arms 26 and 27 adapted to extend rearwardly to the wearer's ears. See, for example, the trunnions 28 or tongue 28a integral with top frame 20, and the bearings or openings 69 in flanges 70 integral with the stem (FIG. 6a). These elements are of molded plastic construction and designed to forcibly interfit and to allow forcible "pull-away," as during impact, for the safety of the wearer. Stems 27 hook at 29 over the wearer's ears and may also consist of molded plastic material.

Referring to FIGS. 1 and 2, a nose piece 30 bounds the upwardly humped lower edge 31 of the pane, and has terminals 32 and 33 which are laterally spaced apart to be located along the edges 31a of the pane. The nose piece has upwardly extending sections 30a which taper toward one another in matching relation to pane edges 31a. An upwardly convex section 30b interconnects the sections 30a. As seen in FIGS. 2 and 4, the nose piece 30 has a slot 34 formed therein to extend along the wave-shaped length of the nose piece to removably engage the upwardly humped lower edge of the pane. FIG. 4a shows the nose piece as channel-shaped in cross section, with flanges 35 and 36 that taper toward one another to be spread apart upon reception of the pane, as seen in FIG. 4, providing a removable grip or retention of these elements. The nose piece typically consists of a relatively soft elastomeric material having a coefficient of sliding friction that increases when the material is wetted. Such a material is hydrophilic and tends to retain the nose piece in position on the wearer's upper nose area as the wearer perspires or encounters moisture, as during skiing. Also, the material is soft for comfort. One such material is KROTON G, a product of Shell Oil Company.

FIGS. 10–12 show the provision of elastomeric pads 70 connected to the nose piece and adapted to flex and closely fit the opposite sides of the wearer's nose. A V-shaped elastomeric connector 71 joins the pads to reinforce them and yieldably resist pad flexing. Connector 71 parallels the nose piece at 30b, and they define a ventilation slot 73 therebetween to pass air to the rear side of the pane 11 bridge section 13 to resist fogging.

The nose piece 30 and attached pads 70 may be removed relatively downwardly and replaced with a selected substitute having different size, shape or color to meet the needs of the wearer. Also, the top frame may be easily removed upwardly from the pane and replaced with a different size or color frame. Alternatively, the pane itself may be replaced with a substitute having different sun blocking shading or composition, color, etc. Thus, the wearer or user may assemble the sunglasses from a large number of different components, as provided on a rack or other display, to result in an assembled sunglasses truly best fitted and best suited, component-wise, in every respect to the requirements of the wearer. One such rack is shown at 40 in FIG. 10 with a number of different panes 11, frames 20 and nose pieces 30 having different size, color, etc., characteristics, but interfittable as described above to provide a custom sunglasses, easily selected, compared and assembled by the wearer or dealer.

The notches or notched areas 21 and 22 that extend downwardly proximate the attachments of the hinged connections of the arms to the top frame also open sidewardly as illustrated in FIG. 6. It is found that such upper notches draw discharge moisture collecting on rearward surfaces of pane and below the top frame (which projects rearwardly from the top of the pane). Such discharge is believed due to an aspirating effect of air directed laterally toward the notches at the front of the pane during forward movement of the wearer (as for example, a skier). Also, air turbulence at the rear side of the pane is reduced due to presence of the notches. Accordingly, the wearer's eyes are further protected from air turbulence and moisture, and during skiing, wind surfing, etc.

The frame 20 also has a second slot 80 sunk in its rearward side (FIG. 9) to receive a tongue portion 81a of a foam pad strip 81. Padding 81 is adapted to engage the wearer's forehead for comfort, whereby the sunglasses are yieldably supported on the wearer's nose by flexing elastomeric pads 70 and by engagement of pad 80 with the wearer's forehead, as during force application to the sunglasses toward the wearer's face.

Although this invention has been described in terms of certain preferred embodiments, other embodiments that are apparent to those of ordinary skill in the art are also within the scope of this invention. Accordingly, the scope of the invention is intended to be limited only by the appended claims.

What is claimed is:

1. Sunglass, comprising:
   (a) a unitary transparent pane adapted to extend in a curved pane in the path of a wearer's field of vision, both frontally and sidewardly;
   (b) a top frame extending along and bounding the elongated upper edge of the pane, the top frame having an elongated slot formed to extend upwardly in the frame from the lower side of the frame, along the frame length, to removably vertically receive and closely fit the upper edge of the pane;
   (c) projections on the pane to interlock with integral portions of the top frame; and
   (d) ear stems removably attached to the top frame at opposite ends thereof, and adapted to extend rearwardly to the wearers ears.

2. Sunglasses, comprising:
   (a) a unitary transparent pane located to extend in a curved pane, plane in the path of a wearer's field of vision, both frontally and sidewardly, the pane having an upwardly humped lower edge bounding a space to receive the wearer's nose;
   (b) a top frame extending along and bounding the elongated upper edge of the pane, the top frame having an elongated slot formed to extend upwardly in the frame from the lower side of the frame, along the frame length, to removably vertically receive and closely fit the upper edge of the pane;
   (c) ear stems attached to the top frame at opposite ends thereof, and adapted to extend rearwardly to the wearer's ears; and
   (d) a nosepiece having a slot therein and extending therealong to removably receive and closely fit the upwardly humped lower edge of the pane,
   wherein the top frame and the nose piece are independently attached to the pane via the slots in the top frame and nose piece to permit selective removal and replacement of the top frame and nose piece, the pane is notched downwardly proximate the attachments of the ear stems to the top frame, the notches opening sidewardly above opposite ends of the pane to draw and discharge moisture collecting on rearward surfaces of the pane during forward movement of the wearer, the top frame overhanging said notches and spaced above notch lower edges, and the pane includes projections overhanging portions of the notches to interlock within end portions of the elongated slots.

3. Sunglasses as defined in claim 2, wherein each stem is pivotally removably attached to an end portion of the frame, the attachment defined by snap interfit members on the frame to allow forcible pull-away of the stem from the frame as during accidental impact.

4. Sunglasses as defined in claim 3, wherein the interfit members have a tongue and groove configuration.

5. Sunglasses as defined in claim 3, wherein the interfit members include upper and lower trunnions on one of the frame and stem, and trunnion receiving bearings on the other of said frame and stem, the trunnions and bearings having sideward interference fit, allowing forcible pull-away as defined.

6. Sunglasses, comprising:
   (a) a unitary transparent pane adapted to extend in a curved pane in the path of a wearer's field of vision, both frontally and sidewardly, the pane having tangs at two locations respectively proximate the upper opposite ends of the pane;
   (b) a top frame extending along and bounding the elongated upped edge of the pane, the top frame having an elongated slot formed to extend upwardly in the frame from the lower side of the frame, along the frame length, to removably vertically receive and closely fit the upper edge of the pane;
   (c) said tangs interlocking within end portions of the slot integral with the top frame; and
   (d) ear stems removably attached to the top frame at opposite ends thereof, and adapted to extend rearwardly to the wearer's ears.

7. Sunglasses as defined in claim 6; wherein the pane is substantially cylindrical.

8. Sunglasses, comprising:
   (a) a unitary transparent pane adapted to extend in a curved pane in the path of a wearer's field of vision, both frontally and sidewardly, the pane having an upper elongated curved edge;
   (b) a top frame extending along and bounding said upper elongated curved edge of said pane, the top frame having an elongated slot formed to extend upwardly in the frame from the lower side of the frame, along the frame length, to removably vertically receive and closely fit said upper elongated curved edge of the pane; and
   (c) extensions on the pane to interlock with integral portions of the top frame to removably secure the lens;
   said elongated slot having a first curvature and said pane upper edge having a second curvature, said slot curvature and said pane upper edge curvature being slightly mismatched to provide means for gripping said pane in said frame.

9. Sunglasses, comprising:
   (a) a unitary, transparent pane adapted to extend in a curved pane in the path of a wearer's field of vision, both frontally and sidewardly, the pane having a curved, elongated upper edge;
   (b) a top frame extending along and bounding the curved, elongated upper edge of said pane, the top frame having an elongated slot formed therein along the frame length to removably vertically receive and closely fit said upper edge of said pane; and
   (c) extensions on the pane to interlock with integral portions of the top frame to removably secure the lens.

* * * * *